(12) United States Patent
Murphy

(10) Patent No.: US 6,468,262 B1
(45) Date of Patent: Oct. 22, 2002

(54) BUOYANT TIP ASPIRATION CATHETER AND METHODS OF USE

(75) Inventor: Richard O. Murphy, Sunnyvale, CA (US)

(73) Assignee: EMBOL-X, Inc., Mountain View, CA (US)

( * ) Notice: Subject to any disclaimer, the term of this patent is extended or adjusted under 35 U.S.C. 154(b) by 0 days.

(21) Appl. No.: 09/454,240

(22) Filed: Dec. 2, 1999

(51) Int. Cl.⁷ .................................... A61M 1/00
(52) U.S. Cl. ................ 604/540; 604/508; 604/510; 600/585
(58) Field of Search .................. 604/270, 528, 604/523, 540, 500, 506–510; 600/585

(56) References Cited

U.S. PATENT DOCUMENTS

| | | | |
|---|---|---|---|
| 4,002,174 A | | 1/1977 | Reed et al. |
| 4,603,699 A | * | 8/1986 | Himpens |
| 4,752,286 A | * | 6/1988 | Okada ...................... 604/96.01 |
| 4,846,174 A | | 7/1989 | Willard et al. |
| 5,151,087 A | * | 9/1992 | Jonkman ...................... 604/164 |
| 5,336,205 A | | 8/1994 | Zenzen et al. |
| 5,554,138 A | * | 9/1996 | Stanford et al. ............. 604/264 |
| 5,709,657 A | * | 1/1998 | Zimmon .................. 604/96.01 |
| 5,730,733 A | | 3/1998 | Mortier et al. |
| 5,795,325 A | | 8/1998 | Valley et al. |
| 5,902,254 A | * | 5/1999 | Magram ...................... 600/585 |
| 5,947,939 A | | 9/1999 | Mortier et al. |
| 6,045,531 A | * | 4/2000 | Davis ...................... 604/96.01 |

* cited by examiner

*Primary Examiner*—Anhtuan T. Nguyen
*Assistant Examiner*—Jeremy Thissell
(74) *Attorney, Agent, or Firm*—Lyon & Lyon LLP

(57) ABSTRACT

A catheter comprising a flexible elongate tubular member having a lumen communicating with a proximal end and a distal port at a distal end. A chamber, filled with gas or fluid less dense than blood, is mounted at the distal end. Methods of using the aspiration catheter for removing embolic air or gaseous bubbles within a body cavity are also disclosed.

16 Claims, 5 Drawing Sheets

BUOYANT TIP ASPIRATION CATHETER AND METHODS OF USE

FIELD OF THE INVENTION

The present invention relates generally to medical devices for aspirating air or gas from a patient's body cavity, such as a vessel or cardiac chamber. More particularly, the devices comprise a catheter having a chamber filled with gas of low density and mounted at a distal end of the catheter. The chamber provides buoyancy to the catheter tip which seeks out and aspirates air or gas in the body cavity.

BACKGROUND OF THE INVENTION

Aspiration catheters are frequently used during surgical or interventional procedures for removing air, fluid, and/or blood from a patient's body cavity. During cardiovascular procedures, such as coronary artery bypass grafting surgery, ventricular septal defect repair, heart valve repair or replacement, ventricular myomectomy (Bautista procedure), septal-myomectomy, aortic aneurysm repair, or aortic thrombectomy, removal of air from a cardiac chamber and/or the aorta is particularly important since distal embolization of air may result in ischemia or infarction of peripheral organs. Treatment of vascular stenosis using endovascular procedures, e.g., angioplasty, stent deployment, or atherectomy, is also associated with increased risk of air embolization resulting in cerebral ischemia or infarction.

Current aspiration catheters are designed to remove fluid in a body cavity. Removal of air, however, is difficult because the air bubbles tend to accumulate against the vessel wall at a position difficult to reach. Thus, air removal is often not complete and patients remain at risk for air embolization.

Thus, there is a need for devices and methods which effectively remove air within a patient's body tissue or cavity during surgical or endovascular procedures.

SUMMARY OF THE INVENTION

The present invention provides a buoyant tip aspiration catheter adapted for insertion into a patient's body cavity. The catheter is most useful in removing air from a cardiac chamber, e.g., the left atrium or left ventricle, and a vessel, including arteries and veins of various sizes. It will be understood that the catheter can also be used in removing air in any other body cavity, e.g., biliary tree.

In a first embodiment, the catheter comprises a flexible elongate tubular member which has a lumen communicating with a proximal and a distal end. The tubular member is made from a thin-walled material, e.g., thermal plastic, polyvinyl chloride, polyolefin, or PEBAX. The distal end includes an aspiration port which communicates with the lumen. A chamber which is filled with a gas, such as helium, hydrogen, or carbon dioxide, is mounted at the distal end. In certain embodiments, the chamber comprises a toroidal or annular balloon or an olive-shaped balloon which communicates with an inflation lumen. In other embodiments, the chamber can have the shape of a sphere or ellipse or any other suitable geometric shape.

In another embodiment, the catheter is insertable through an introducer, such as a cannula. The proximal end of the catheter is connected to a pump which applies negative pressure to the lumen. In certain embodiments, a small wire is helically wound within the catheter to prevent kinking.

In a first method of using the aspiration catheter disclosed herein for removing gas from fluid or blood within a body cavity, the distal end of the catheter is inserted through an incision in tissue, such as a vessel. The distal end is directed to and seeks out the location of gas within the body cavity by the buoyant chamber. The gas is then removed from the body cavity through the distal port and lumen under suction. During cardiovascular surgeries, such as heart valve repair or replacement, removal of gaseous material from the cardiac chambers and aorta reduces a patient's risk of perioperative complication, such as neurocognitive, e.g., stroke and delirium.

It will be understood that there are several advantages in using the aspiration catheters and methods disclosed herein for treating a vascular lesion. For example, the catheters (1) can be inserted in arteries or veins of various diameter, (2) provide near-total capture of embolic gaseous bubbles, thereby dramatically reducing the risk of distal embolization, and (3) are insertable through an introducer and can be used with other endovascular devices.

DETAILED DESCRIPTION

Figure 1A:
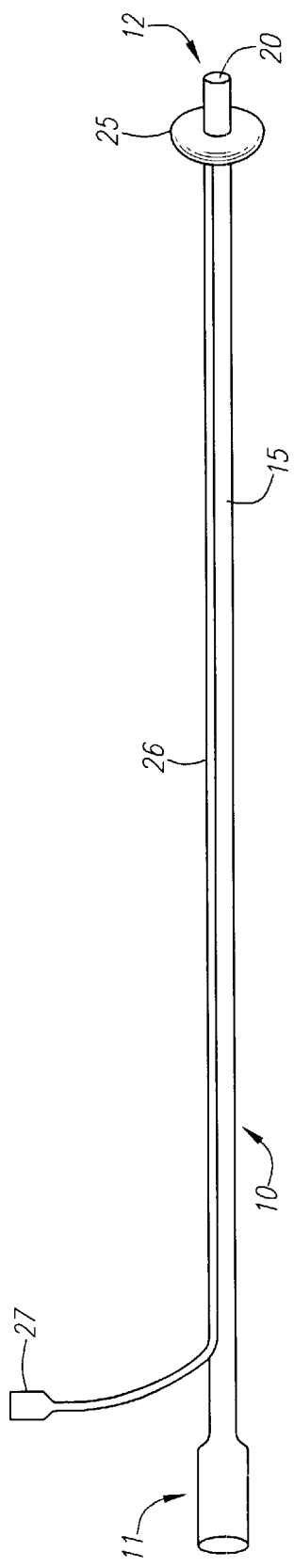
FIG. 1A depicts an embodiment of the aspiration catheter for removing gas within a body cavity according to the present invention.

Referring now to the drawings, an embodiment of the aspiration catheter for removing gas within a body cavity is depicted in FIG. 1A. The catheter comprises a flexible elongate tubular member 10 which has lumen 15 communicating with proximal end 11 and distal port 20 at distal end 13. Toroidal balloon 25, which communicates with inflation lumen 26 and inflation port 27, is mounted at distal end 12. Balloon 25 can be expanded by infusing air, gas, or other fluid less dense than blood into the inflation lumen port 27 and lumen 26 to provide buoyancy to the catheter tip.

Figure 1B:
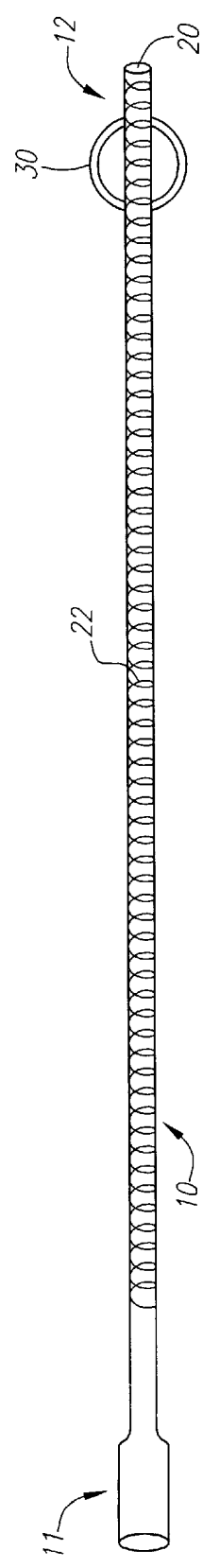
FIG. 1B depicts another embodiment of the aspiration catheter having an olive-shaped distal end.

Another embodiment of the aspiration catheter having olive-shaped chamber 30 at distal end 12 is shown in FIG. 1B. Chamber 30 is filled with gas or foam to provide buoyancy to the catheter tip. Tubular member 10 also includes helical wire 22 in its wall to provide increased flexibility and prevent kinking of the catheter.

Figure 1C:
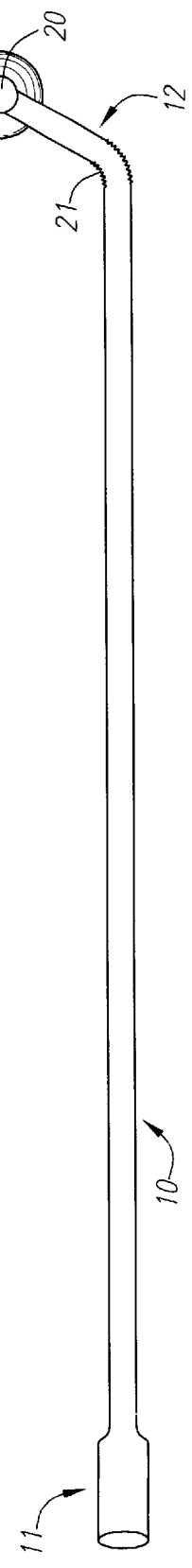
FIG. 1C depicts another embodiment of the aspiration catheter having an angled distal end.

FIG. 1C depicts another embodiment of the aspiration catheter which has distal end 12 angled relative to proximal end 11 at flexible region 21 to facilitate removal of gas within a vessel. When the catheter is inserted through an introducer or cannula, distal end 12 and proximal end 11 assume a linear configuration at region 21. Annular balloon 30 is mounted on distal end 12 to provide buoyancy to the catheter tip.

Figure 2:
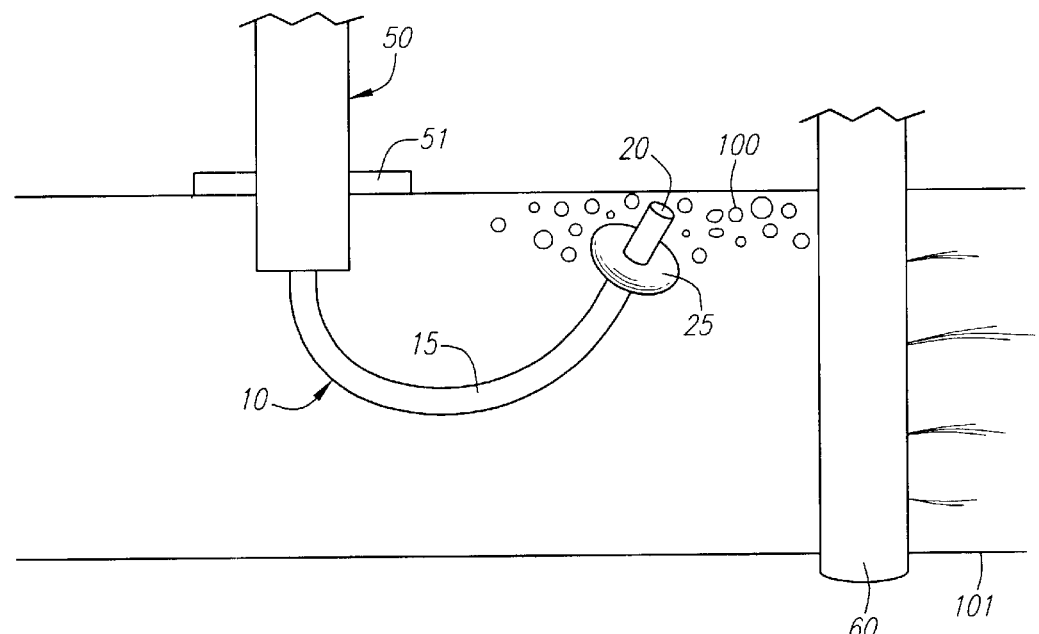
FIG. 2 depicts the catheter of FIG. 1A inserted in the aorta.

In using the aspiration catheter of FIG. 1A to remove gas or air within aorta 101, for example, distal end 12 is inserted through the lumen of cannula 50 as depicted in FIG. 2. During cardiopulmonary bypass, coronary blood flow is isolated from the peripheral circulation by placement of aortic clamp 60 across aorta 101. Aortic cannula 50 is often inserted downstream of clamp 60 to perfuse the peripheral organs, including the brain. Insertion of cannula 50, which includes suture flange 51, often introduces air or gas 100 within the aorta. The gas or air rises to the vessel wall and is difficult to remove by use of a conventional aspiration catheter. By inserting the catheter described herein having toroidal balloon 25 mounted at distal end 12 into aorta 101, the gas or fluid inside balloon 25 allows distal end 12 to be buoyant compared to blood and to rise to the location of gas 100. The proximal end of the catheter is then attached to a vacuum and gas 100 is removed through port 20 and lumen 15 of the catheter under negative pressure. In this way, near complete removal of air 100 can be achieved, and distal embolization of gas can be minimized when aortic clamp 60 is removed to re-established aortic flow. Alternatively, the catheter can also be used to aspirate other embolic debris, e.g., calcium, thrombi, atheromatous plaque, and/or tissue debris, by deflating balloon 25 by removing gas or fluid from its inflation lumen.

Figure 3:
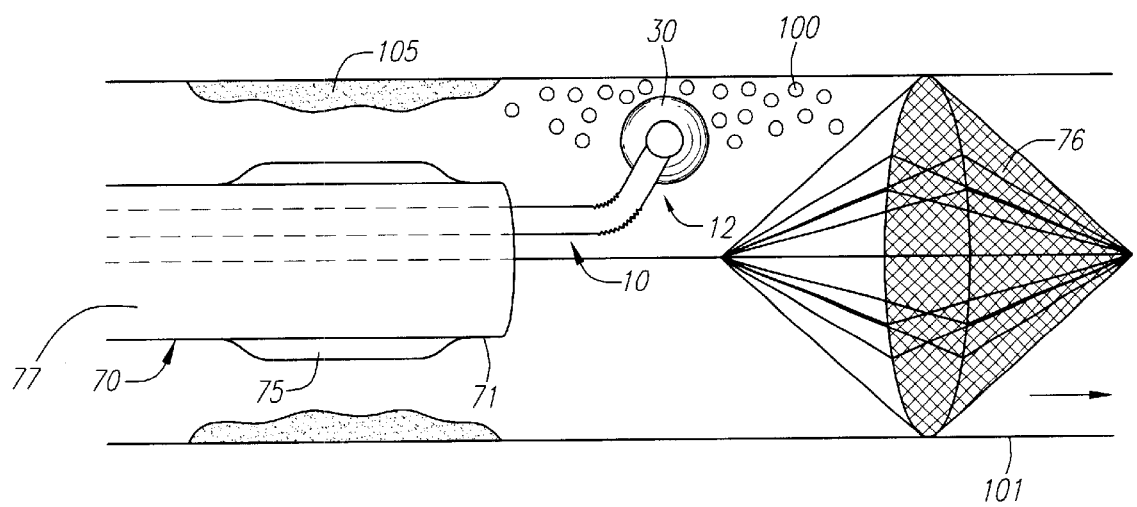
FIG. 3 depicts the catheter of FIG. 1C inserted through an angioplasty catheter.

The aspiration catheters disclosed herein can also be used to remove air or gas during endovascular procedures, e.g., angioplasty, atherectomy, or stent deployment. In FIG. 3, the catheter of FIG. 1C is inserted through lumen 77 of angioplasty catheter 70. In removing atheromatous lesion 105 in aorta 101, for example, filter 76 is inserted downstream of lesion 75 to provide protection against distal embolization. However, the protection is often incomplete. After lumenal patency is re-established by expanding angioplasty balloon 75 mounted at distal end 71 of angioplasty catheter 70, distal end 12 of the aspiration catheter is inserted through lumen 77 of catheter 70. The distal end and proximal end of tubular member 10 assume a linear configuration during its insertion within catheter 70. When the aspiration catheter is deployed in aorta 101, distal end 12 is angled relative to the proximal end. The angled configuration and relatively buoyant annular balloon 30 guide the catheter tip to gas 100. After gas 100 is removed under suction from the aspiration catheter, angioplasty catheter 70 and catheter 10 are removed. Filter 76 is then collapsed and, with the entrapped embolic debris, is removed.

Figure 4:
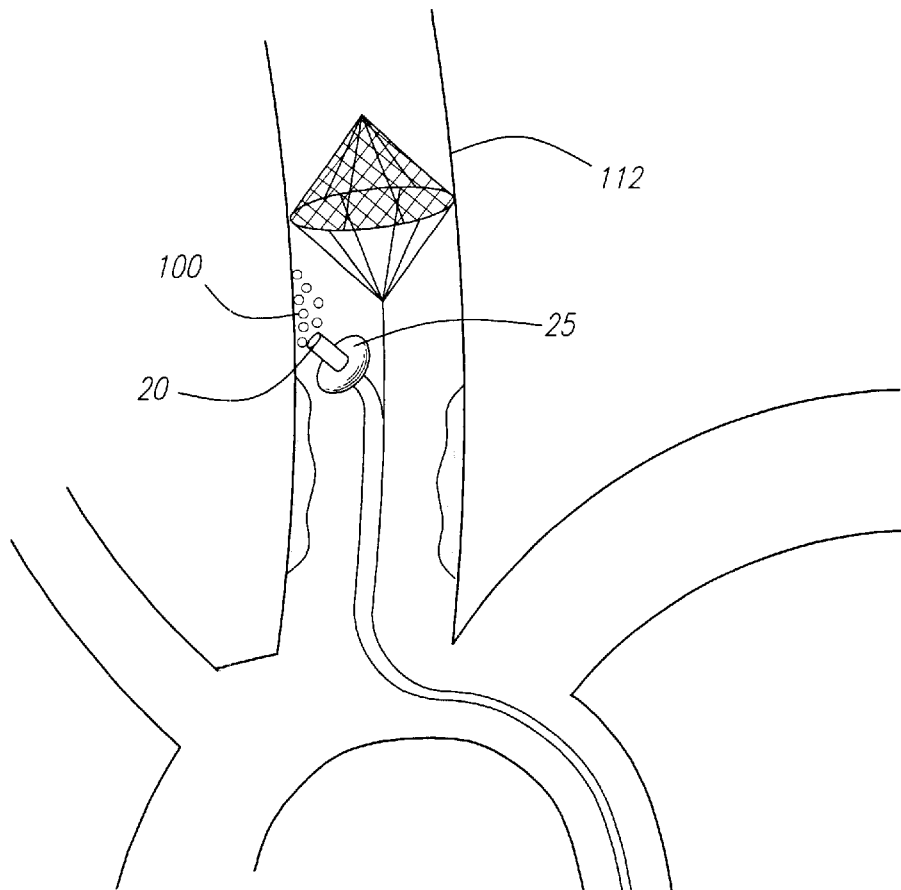
FIG. 4 depicts the catheter of FIG. 1A inserted into the left common carotid artery.
Figure 4:
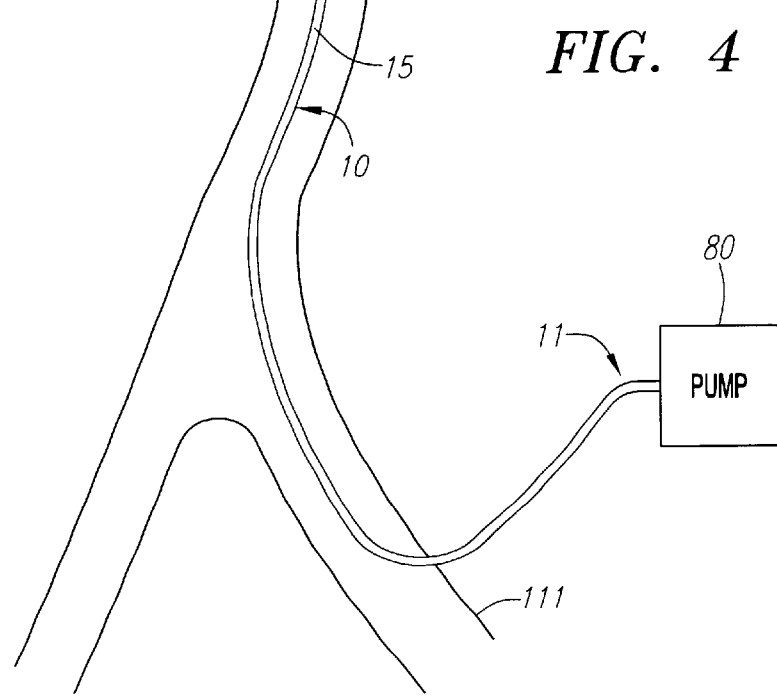

Removal of embolic air or gaseous bubbles is particularly important in carotid procedures, such as carotid endarterectomy or angioplasty. Air embolization is a common cause of stroke or cerebral ischemia. FIG. 4 depicts the catheter of FIG. 1A inserted through left femoral artery 111 into left common carotid artery 112 during endovascular procedures. The catheter may carry filter 76 at a distal end to be placed downstream. Alternatively, the filter can be replaced by an occluder or a vessel clamp. Proximal end 11 of the catheter is connected to pump 80 which provides suction to lumen 15 and port 20 for removal of gas or air 100 generated within left common carotid artery during endovascular procedures. Alternatively, gas is removed from the vessel by reason of the pressure differential between blood pressure inside the vessel and atmospheric pressure outside the vessel. Where the system relies on this pressure differential, no external pump is needed.

Figure 5A:
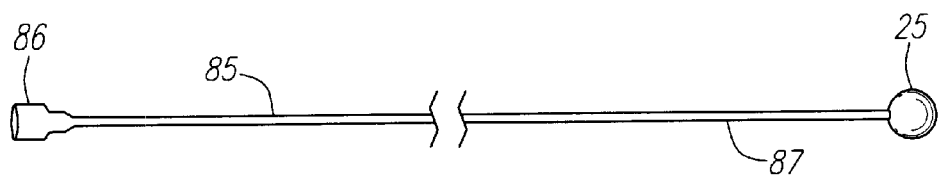
FIG. 5A depicts a guidewire having a gas-filled chamber at a distal end.
Figure 5B:
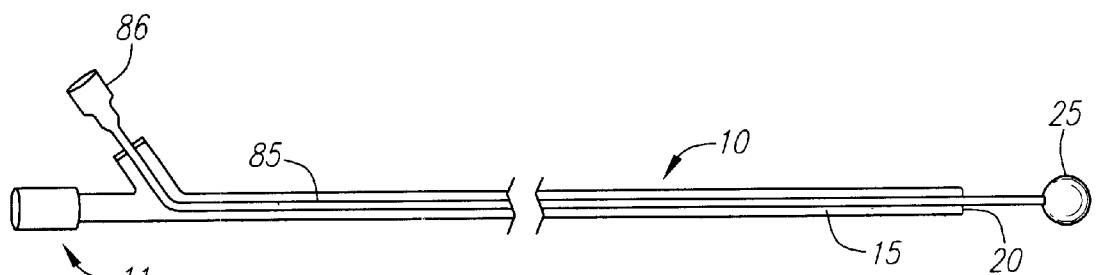
FIG. 5B depicts the guidewire of FIG. 5A disposed within a catheter.
Figure 5C:
FIG. 5C depicts the catheter of FIG. 5B having an additional infusion lumen.
Figure 5D:
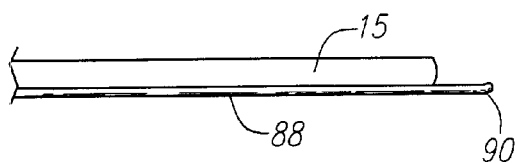
FIG. 5D depicts the catheter of FIG. 5C having a curved distal infusion tip.

The buoyant chamber may be integral with the aspiration catheter as described above, or mounted on a separately insertable guidewire as shown in FIGS. 5A through 5D. In FIG. 5A, guidewire 85 has chamber 25 mounted at a distal end. Chamber 25 communicates with lumen 87, which communicates with infusion port 86 at a proximal end of guidewire 85. In an alternative construction, chamber 25 is pre-filled, and does not require an inflation lumen. FIG. 5B shows guidewire 85 disposed within lumen 15 of aspiration catheter 10. FIG. 5C shows aspiration catheter 10 having proximal infusion port 89 communicating with infusion lumen 88, which in turn communicates with distal infusion port 90. FIG., 5D shows another embodiment of distal infusion port 90 having a curved construction. The jet of fluid, e.g. saline or Ringer's lactate, delivered by infusion port 90 creates vortex flow for enhancement of aspiration.

Figure 6:
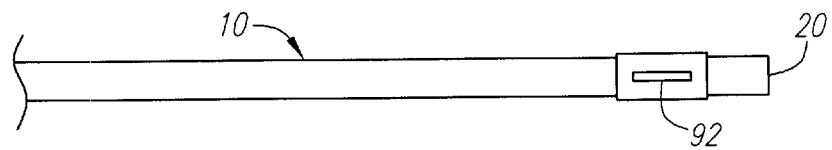
FIG. 6 depicts a catheter having a finned rotating chamber at a distal end.

FIG. 6 depicts another embodiment of aspiration catheter 10 having one or more finned rotating member 92 included at its distal end. The number of fins can range from 2 to 10 or more, and typically 3–5 fins are used. The finned rotating member causes turbulence in the heart chamber and the aorta, thereby mixing air or gaseous emboli with blood to facilitate aspiration.

Figure 7A:
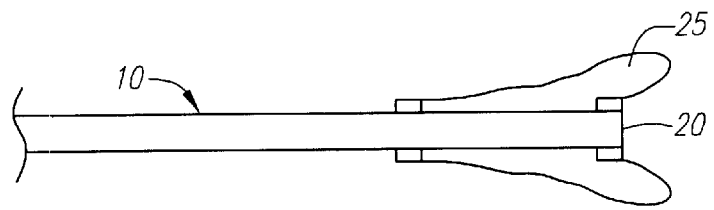
FIG. 7A depicts another embodiment of the aspiration catheter having a deflated balloon.
Figure 7B:
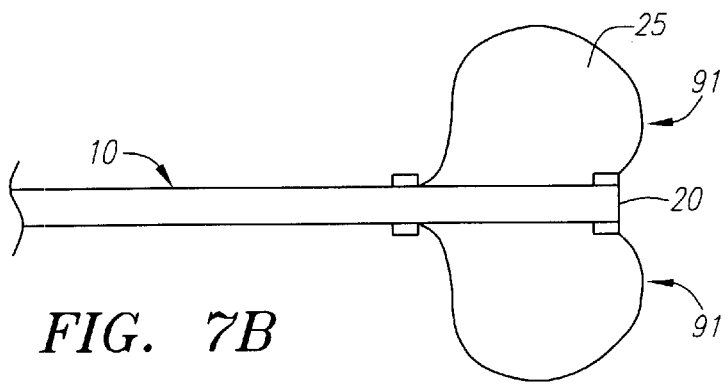
FIG. 7B depicts the aspiration catheter of FIG. 7A having an inflated balloon.

FIGS. 7A and 7B depict another embodiment of the distal end of aspiration catheter 10. FIG. 7A shows balloon 25 deflated. FIG. 7B shows inflated balloon 25. Notably, the distal most edge of balloon 25, shown here as 91, extends distally beyond distal port 20 of aspiration catheter 10.

Figure 8:
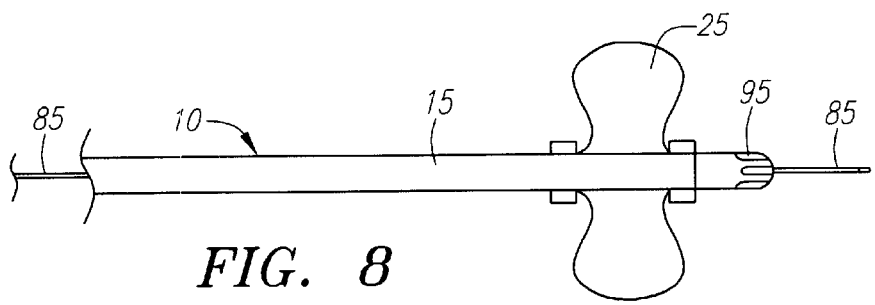
FIG. 8 depicts a guidewire disposed within a catheter having vented aspiration ports.
Figure 9:
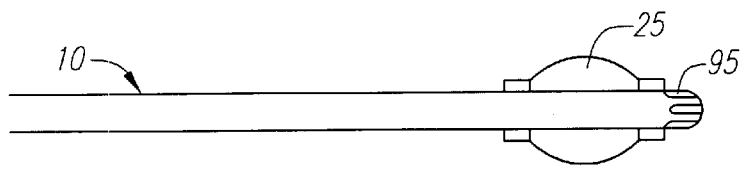
FIG. 9 depicts another embodiment of the aspiration catheter having vented aspiration ports.

FIG. 8 shows alternative catheter 10 having a plurality of distal vents 95 which comprise the aspiration ports. Optionally, guidewire 85 extends through lumen 15 of catheter 10 and distally beyond vents 95. FIG. 9 shows an olive-shaped balloon 25 mounted on the distal end of catheter 10 having vents 95 for aspiration of gas.

The length of the aspiration catheter will generally be between approximately 20 and 100 centimeters, preferably between approximately 40 and 60 centimeters. The inner diameter of the aspiration catheter will generally be between approximately 0.1 and 0.3 centimeters, preferably approximately 0.15 and 0.2 centimeters. The outer diameter of the toroidal or annular balloon will generally be between approximately 0.1 and 0.8 centimeters, preferably approximately 0.2 and 0.5 centimeters. The foregoing ranges are set forth solely for the purpose of illustrating typical device dimensions. The actual dimensions of a device constructed according to the principles of the present invention may obviously vary outside of the listed ranges without departing from those basic principles.

Although the foregoing invention has, for purposes of clarity of understanding, been described in some detail by way of illustration and example, it will be obvious that certain changes and modifications may be practiced which will still fall within the scope of the appended claim. It will also be understood that each feature of each embodiment discussed herein, and of each reference cited herein, can be used in combination with the features of any other embodiment.

What is claimed is:

1. A method for removing gas from blood within a body cavity, comprising the steps of:

providing a buoyant tip catheter comprising a flexible elongate tubular member having a proximal end, a distal end, and a lumen therebetween, the distal end having a port communicating with the lumen, the elongate tubular member further comprising a chamber mounted at the distal end and filled with a first gas;

inserting the elongate tubular member into the body cavity;

advancing the distal end of the elongate tubular member to a location in the vicinity of a second gas;

allowing the first gas-filled chamber mounted at the distal end of the elongate tubular member to seek out the second gas; and removing the second gas from the body cavity.

2. The method of claim 1, wherein the second gas is removed from a vessel.

3. The method of claim 2, wherein the vessel is the aorta.

4. The method of claim 2, wherein the second gas is removed by reason of a pressure differential between the inside and outside of the vessel.

5. The method of claim 1, wherein the second gas is removed from a cardiac chamber.

6. The method of claim 5, wherein the cardiac chamber is the left atrium.

7. The method of claim 1, wherein the second gas is removed under a negative pressure applied to the lumen of the elongate tubular member.

8. The method of claim 1, further comprising the step of performing a valve repair procedure.

9. The method of claim 1, further comprising the step of performing an open-heart intracardiac procedure.

10. The method of claim 9, wherein the intracardiac procedure comprises septal-myomectomy.

11. The method of claim 1, wherein the distal end of the elongate tubular member is inserted into the aorta and directed through the aortic valve into the heart.

12. A method for removing gas from blood within a body cavity, comprising the steps of:

inserting a catheter into the body cavity, the catheter having a proximal end, a distal end, and a lumen therebetween, the distal end having a port communicating with the lumen;

inserting a guidewire through the lumen of the catheter, the guidewire comprising a chamber mounted at a distal end of the guidewire and filled with a first gas;

advancing the distal end of the catheter and guidewire to the location in the vicinity of a second gas;

allowing the first gas-filled chamber mounted at the distal end of the guidewire to seek out the second gas; and removing the second gas from the body cavity.

13. The method of claim 12, wherein the guidewire further includes an inflation lumen communicating with the chamber.

14. The method of claim 12, wherein the catheter further includes aspiration enhancement capabilities.

15. The method of claim 14, wherein the aspiration enhancement capabilities comprise an infusion lumen communicating with an outlet near the aspiration port.

16. The method of claim 12, wherein the catheter further comprises a second lumen.

* * * * *